United States Patent
Kinoshita et al.

(10) Patent No.: US 7,196,241 B2
(45) Date of Patent: Mar. 27, 2007

(54) SANITARY NAPKIN WITH COMPRESSED GROOVES

(75) Inventors: Masataka Kinoshita, Kagawa (JP); Kazuya Nishitani, Kagawa (JP); Toshiyuki Tanio, Kagawa (JP); Akane Sakai, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 162 days.

(21) Appl. No.: 10/841,386

(22) Filed: May 7, 2004

(65) Prior Publication Data

US 2004/0243082 A1      Dec. 2, 2004

(30) Foreign Application Priority Data

May 29, 2003   (JP)   ............................. 2003-152000

(51) Int. Cl.
  *A61F 13/15*   (2006.01)
(52) U.S. Cl. ............ 604/380; 604/385.01; 604/385.03; 604/387
(58) Field of Classification Search ................ 604/379, 604/380, 385.01, 385.03, 385.24, 386, 387
  See application file for complete search history.

(56) References Cited

U.S. PATENT DOCUMENTS

| 5,941,861 | A * | 8/1999 | Ng ............................... 604/366 |
| 6,159,190 | A * | 12/2000 | Tanaka et al. .......... 604/385.24 |
| 6,210,385 | B1 * | 4/2001 | Mizutani ................ 604/385.01 |
| 6,326,525 | B1 * | 12/2001 | Hamajima et al. ........... 604/378 |
| 6,371,948 | B1 * | 4/2002 | Mizutani ................ 604/385.01 |
| 7,122,713 | B2 * | 10/2006 | Komatsu et al. ............ 604/380 |
| 2004/0243087 | A1 * | 12/2004 | Kinoshita et al. ....... 604/385.04 |
| 2004/0249355 | A1 * | 12/2004 | Tanio et al. ............ 604/385.01 |
| 2004/0260262 | A1 * | 12/2004 | Nishitani et al. ....... 604/385.04 |
| 2004/0260263 | A1 * | 12/2004 | Tamagawa et al. ..... 604/385.04 |
| 2005/0124951 | A1 * | 6/2005 | Kudo et al. .................. 604/380 |
| 2005/0148970 | A1 * | 7/2005 | Kudo et al. .................. 604/378 |
| 2005/0148971 | A1 * | 7/2005 | Kuroda et al. ............... 604/380 |
| 2005/0148972 | A1 * | 7/2005 | Miyama et al. ............. 604/380 |
| 2005/0148973 | A1 * | 7/2005 | Tamura et al. .............. 604/380 |

FOREIGN PATENT DOCUMENTS

| EP | 1 269 950 A2 * | 1/2003 |
| JP | 08-322879 A1 | 12/1996 |
| JP | 10-328232 A1 | 12/1998 |
| JP | 2000-189458 A1 | 7/2000 |
| JP | 2000-189459 A1 | 7/2000 |

(Continued)

*Primary Examiner*—Tatyana Zalukaeva
*Assistant Examiner*—Michael G. Bogart
(74) *Attorney, Agent, or Firm*—Darby & Darby

(57) ABSTRACT

A sanitary napkin in which diffusing liquid hardly reaches a rear end edge is adapted to make a liquid absorbent layer less deformable in a rear region so that it can easily be kept in close contact with the wearer's buttocks. The sanitary napkin has an elongated main absorbent region surrounded by compressed grooves that are formed in a skin-side surface. Since a rear end of the main absorbent region is far away from a rear end edge of the napkin to provide a relatively large rear region, worries about rearward leakage may be relieved. Furthermore, since auxiliary longitudinal grooves are provided in the rear region, a liquid absorbent layer may hardly be twisted.

7 Claims, 4 Drawing Sheets

FOREIGN PATENT DOCUMENTS

| | | |
|---|---|---|
| JP | 2002-524148 A1 | 8/2000 |
| JP | 2000-288025 A1 | 10/2000 |
| JP | 2001-095842 A1 | 4/2001 |
| JP | 2002-000656 A1 | 1/2002 |
| JP | 2002-065741 A1 | 3/2002 |
| JP | 2002-095697 A1 | 4/2002 |

* cited by examiner

SANITARY NAPKIN WITH COMPRESSED GROOVES

CROSS-REFERENCE TO RELATED APPLICATIONS

The present application claims priority under 35 U.S.C. §119 to Japanese Patent Application No. 2003-152000 filed on May 29, 2003, the entire contents of which being hereby incorporated herein by reference.

BACKGROUND OF THE INVENTION

1. Field of the Invention

The present invention relates to an elongated sanitary napkin suitable for nighttime use. More particularly, the invention relates to a sanitary napkin in which an absorbent region is defined by compressed grooves formed in its skin-side surface.

2. Description of the Related Art

Elongated sanitary napkins of the type having an elongated absorbent region that is surrounded by a compressed groove formed in its skin-side surface have been known as being suitable for nighttime use.

For example, Japanese Unexamined Patent Publication No. 2001-95842 (Patent Publication1) and Japanese Unexamined Patent Publication No. 2002-656 (Patent Publication 2) disclose elongated sanitary napkins each having longitudinally extending leakage preventing walls disposed on right and left sides of the skin-side surface. In the region between the right and left leakage preventing walls, an elongated absorbent region is surrounded by a compressed groove. The compressed groove is formed by compressing a liquid absorbent layer together with a liquid-permeable topsheet appearing on the skin-side surface.

In sanitary napkin of this kind, since the absorbent region surrounded by the compressed groove is raised toward the skin-side, the absorbent region can easily be kept in close contact with the vaginal opening of a woman, facilitating rapid absorption of body liquid such as menstrual blood that will be discharged from the vaginal opening over and over again. In addition, since densities of the topsheet and the liquid absorbent layer are increased in the compressed groove, liquid applied to the absorbent region, which tends to spread in all directions through diffusion inside the topsheet and the liquid absorbent layer, may be drawn into the high-density compressed groove and then diffused along the compressed groove, effectively preventing liquid diffusion out of the absorbent region.

In the sanitary napkins disclosed in Patent Publications 1 and 2, not only the main body but also the absorbent region surrounded by the compressed groove is elongated so that the rear end of the absorbent region is located close to the rear end edge of the sanitary napkin. In the elongated sanitary napkins, since the absorbent region is thus elongated, the raised absorbent region may face the wearer's body from the anus to the cleft of the buttocks so that body liquid such as menstrual blood trying to flow down the wearer's body from the anus to the cleft of the buttocks during sleep can easily be received by the rear portion of the absorbent region.

However, if the absorbent region surrounded by the compressed groove extends close to the rear end edge of the main body, as disclosed in Patent Publications 1 and 2, body liquid such as menstrual blood having diffused rearward in the absorbent region may also come close to the rear end edge of the main body. Accordingly, when viewed from the skin-side, the sanitary napkin may look as if a large amount of menstrual blood was applied thereto, easily causing a wearer anxiety about leakage from the rear end edge of the main body.

Also in the elongated sanitary napkin, when its front portion fixed on a crotch part of an undergarment is brought into contact with the vaginal opening, this contact portion will be deformed to bulge toward the vaginal opening due to pressure from the thighs. On the other hand, the rear portion of the sanitary napkin will partially fit in the cleft of the buttocks, while the remaining large portion will be brought into contact with the convex surfaces of the buttocks. However, if the compressed groove surrounding the absorbent region extends close to the rear end edge of the main body, as disclosed in Patent Publications 1 and 2, the rear portion of the sanitary napkin may be too stiff to conform to the curved surfaces of the buttocks. As a result, a space may easily be formed between the rear portion and the wearer's buttocks, for example, such that the rear end edge on the longitudinal centerline and thereabout may easily move away from the wearer's skin.

In this regard, the distance between the rear end of the absorbent region surrounded by the compressed groove and the rear end edge of the main body may be increased to ensure a large region where menstrual blood is difficult to diffuse rearward of the absorbent region. However, if the region having no compressed groove is enlarged in the rear portion of the sanitary napkin, since the liquid absorbent layer can move relatively freely in that region, the liquid absorbent layer in the rear portion may be displaced due to body movement during sleep or the sanitary napkin may be wrinkled due to twisting of the front portion, easily causing problems of deteriorating contact between the skin-side surface and the buttocks and giving an uncomfortable feeling to the buttocks.

SUMMARY OF THE INVENTION

The present invention has been worked out in view of the shortcomings in the prior art set forth above. It is therefore an object of the present invention to provide a sanitary napkin in which a rear region rearward of a main absorbent region is hardly twisted but easily deformed to conform to the buttocks.

According to the present invention, there is provided a sanitary napkin comprising:

an elongated main body having a skin-side surface and a garment-side surface and including a liquid-permeable topsheet appearing on the skin-side surface, a backsheet appearing on the garment-side surface and a liquid absorbent layer disposed between the topsheet and the backsheet; and leakage preventing walls disposed at equal distances on each side of a longitudinal centerline of the main body and extending longitudinally of the main body, the leakage preventing walls exhibiting an elastic contractive force so as to rise from the skin-side surface, compressed grooves where the liquid absorbent layer is compressed together with the topsheet being formed in a region of the main body between the leakage preventing walls, the compressed grooves comprising:

primary longitudinal grooves disposed at equal distances on each side of the longitudinal centerline of the main body, the primary longitudinal grooves extending longitudinally of the main body and defining a main absorbent region therebetween;

a primary transverse groove disposed between rear portions of the primary longitudinal grooves, the primary transverse groove extending transversely of the main body and defining a rear end of the main absorbent region; and auxiliary longitudinal grooves disposed at equal distances on each side of the longitudinal centerline of the main body, wherein the liquid absorbent layer has a rear end edge in a rear region that extends rearward from the rear end of the main absorbent region to a rear end edge of the main body, and the auxiliary longitudinal grooves extend longitudinally of the main body from regions transversely adjacent the main absorbent region to the rear region so that the auxiliary longitudinal grooves in the rear region are transversely spaced more than the primary longitudinal grooves.

In the sanitary napkin according to the present invention, the liquid absorbent layer extends rearward across the rear end of the main absorbent region into the rear region, and the main absorbent region is spaced a distance away from the rear end edge of the main body. Hence, even when body liquid such as menstrual blood diffuses and reaches the rear end of the main absorbent region, a region where liquid diffusion is difficult still remains rearward of it, so that a wearer may hardly feel anxiety about rearward liquid leakage. Moreover, since the right and left auxiliary longitudinal grooves are widely spaced in the rear region, the liquid absorbent layer can be effectively prevented from being displaced or twisted in the rear region. Still moreover, since the rear portion of the sanitary napkin may easily be folded at the widely spaced auxiliary longitudinal grooves, it can easily conform to the curved surfaces of the buttocks.

Preferably, the individual auxiliary longitudinal grooves in the rear region extend parallel to the longitudinal centerline so that the rear region can easily conform to the curved surfaces of the buttocks.

Also preferably, rear ends of the leakage preventing walls are located at substantially the same longitudinal position as or forward of the rear end of the main absorbent region. If the rear ends of the leakage preventing walls are located forward of the rear end of the main absorbent region, the rear region will not be strongly affected by an elastic contractive force of the leakage preventing walls, so that the rear region can easily conform to the curved surfaces of the buttocks.

The compressed grooves may further comprise an auxiliary transverse groove disposed rearward of the primary transverse groove and between the auxiliary longitudinal grooves, wherein a rearward diffusion suppressing region rearward of the rear end of the main absorbent region may be defined between the primary transverse groove and the auxiliary transverse groove, and the auxiliary longitudinal grooves may have rear ends rearward of a rear end of the rearward diffusion suppressing region. With the rearward diffusion suppressing region, anxiety about leakage rearward from the main absorbent region can be reduced more effectively. In this case, the rear ends of the leakage preventing walls are preferably located at substantially the same longitudinal position as or forward of the rear end of the rearward diffusion suppressing region.

The sanitary napkin according to the present invention may further comprise: fold-back flaps projecting outward from transversely opposite sides of the main body and intended to be folded back against an outer surface of an undergarment at a crotch part thereof; and rear flaps located rearward of the fold-back flaps, projecting outward from the transversely opposite sides of the main body and intended to be placed on an inner surface of the undergarment in an unfolded state, wherein the rear flaps may be located outside the auxiliary longitudinal grooves. With the rear flaps located outside the auxiliary longitudinal grooves, the rear portion of the sanitary napkin can easily be deformed to cover a large area of the buttocks.

In the present invention, also preferably, L1/L0 is at least $2/3$, where L0 represent a length from the rear end of the main absorbent region to the rear end edge of the liquid absorbent layer while L1 represents a length from the rear end of the main absorbent region to rear ends of the auxiliary longitudinal grooves. Here, L0 is preferably equal to or greater than 50 mm.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

It should be noted that the sanitary napkin, as well as its individual components, has two major surfaces: of which one surface intended to be worn toward the wearer's crotch is referred to as "skin-side surface", while the other surface is referred to as "garment-side surface". It should also be noted that unless otherwise stated, the term "length" as used herein refers to a dimension measured longitudinally of the sanitary napkin and the term "width" as used herein refers to a dimension measured transversely of the sanitary napkin.

Figure 1:
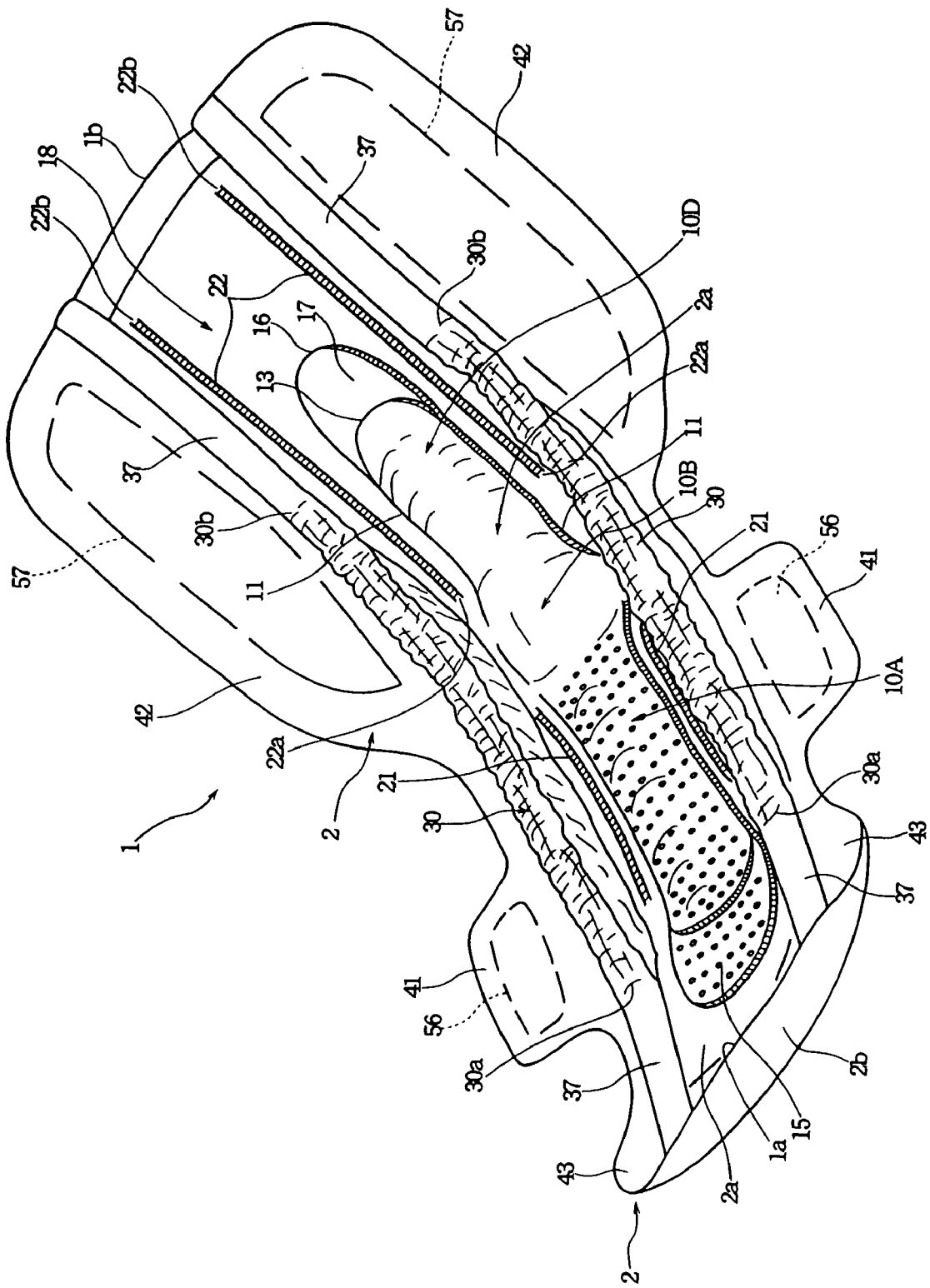
FIG. 1 is a perspective view of a sanitary napkin according to a first embodiment of the present invention.
Figure 2:
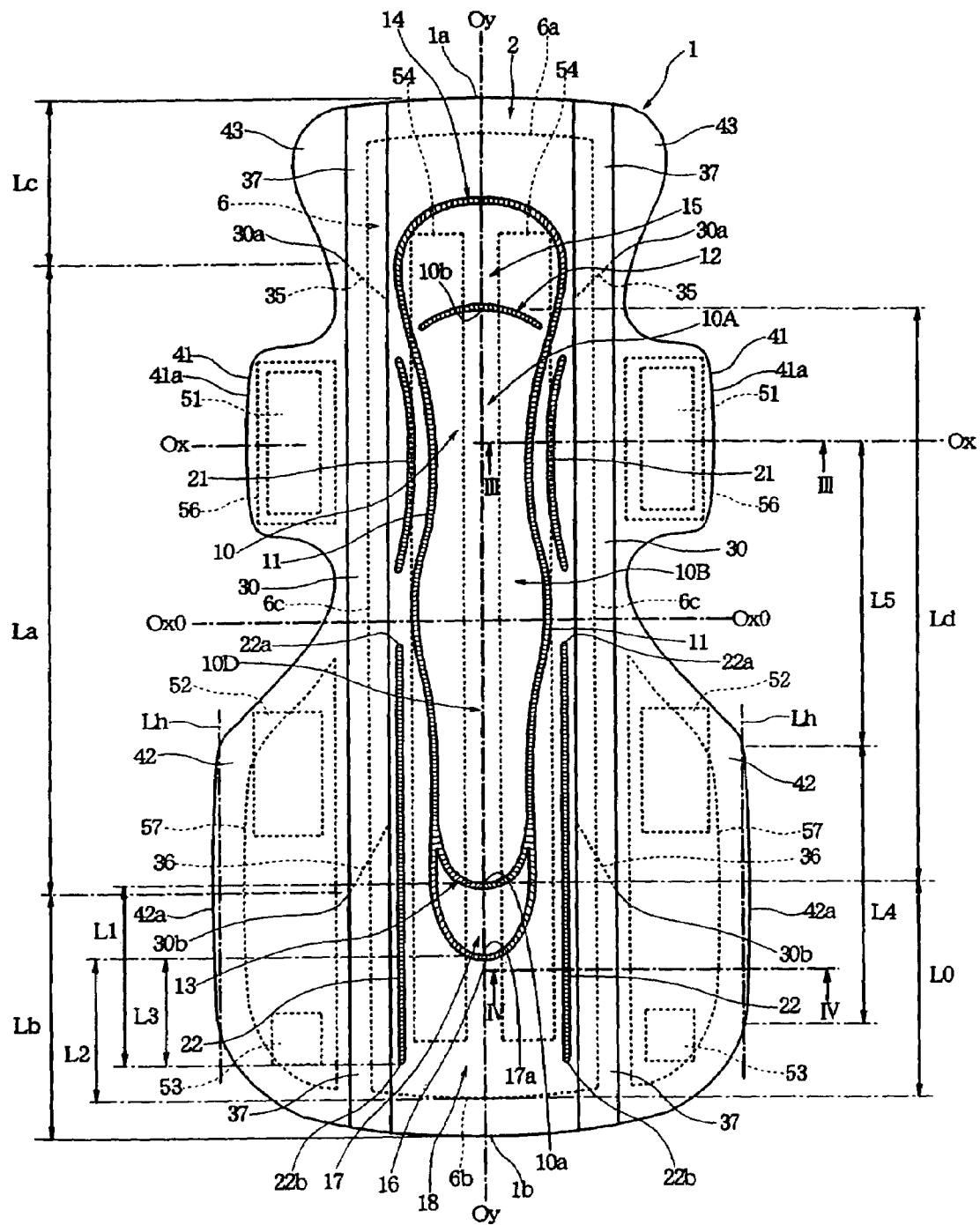
FIG. 2 is a top plan view of the sanitary napkin according to the first embodiment.
Figure 3:
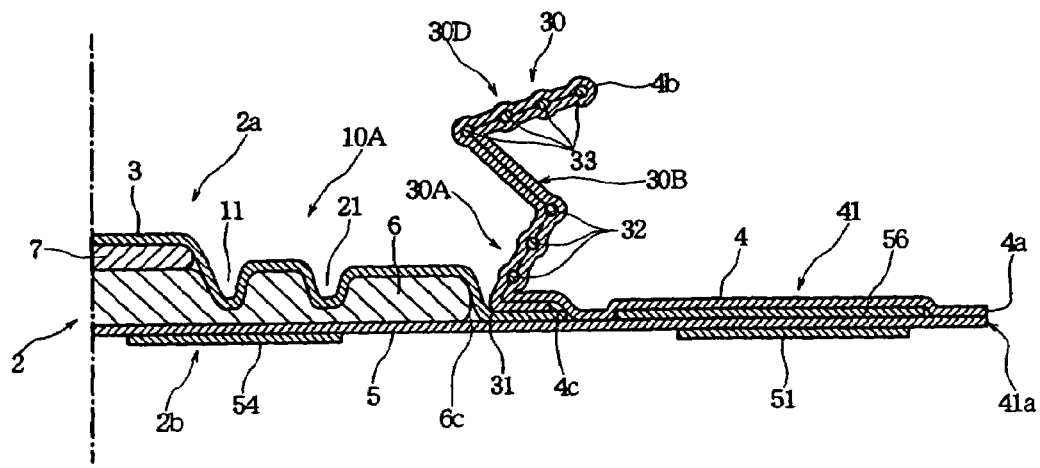
FIG. 3 is a half sectional view taken along line III—III of FIG. 2.
Figure 4:
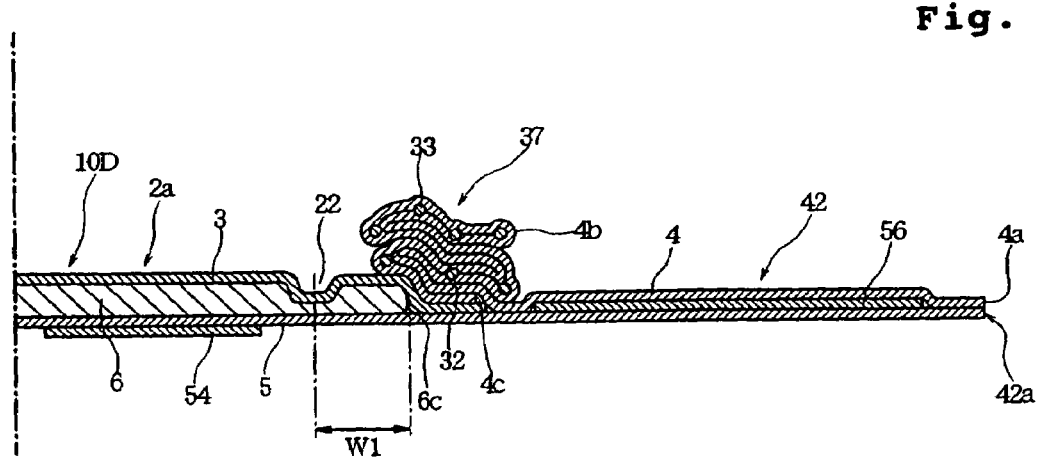
FIG. 4 is a half sectional view taken along line IV—IV of FIG. 2.

FIG. 1 is a perspective view of a sanitary napkin 1 according to a first embodiment of the present invention; FIG. 2 is a top plan view of the sanitary napkin 1; FIG. 3 is a half sectional view taken along line III—III of FIG. 2; and FIG. 4 is a half sectional view taken along line IV—IV of FIG. 2.

According to the first embodiment shown in FIGS. 1–4, the sanitary napkin 1 comprises: an elongated main body 2 having a skin-side surface 2a and a garment-side surface 2b; and a pair of leakage preventing walls 30, 30 that are allowed to rise from the skin-side surface 2a of the main body 2.

In FIG. 2, the sanitary napkin 1, which is slightly curved in FIG. 1, is shown in a fully opened (or flattened) state. FIG. 2 shows a longitudinal centerline Oy—Oy coinciding with midpoints of front and rear end edges 1a, 1b of the sanitary napkin 1, wherein the sanitary napkin 1 has bilateral symmetry about the longitudinal centerline Oy—Oy.

FIG. 2 also shows a transverse reference line Ox—Ox and a transverse centerline Ox0—Ox0 which are both perpendicular to the longitudinal centerline Oy—Oy. The sanitary napkin 1 is intended to be worn with the skin-side surface 2a facing the crotch of a woman so that the intersection between the longitudinal centerline Oy—Oy and the transverse reference line Ox—Ox faces the woman's vaginal opening. The transverse centerline Ox0—Ox0 longitudinally divides the main body 2 into two parts (front and rear portions), and the intersection between the longitudinal centerline Oy—Oy and the transverse centerline Ox0—Ox0 faces the anus or a region slightly posterior to the anus.

As shown in FIGS. 3 and 4, a liquid-permeable topsheet 3 appears on the skin-side surface 2a of the main body 2, in a region between the leakage preventing walls 30, 30; a side sheet 4 appears outside each leakage preventing wall 30. In the present embodiment, the side sheet 4 forms the leakage preventing wall 30. On the other hand, a liquid-impermeable backsheet 5 appears on the garment-side surface 2b of the main body 2.

In the region between the leakage preventing walls 30, 30, the main body 2 has a liquid absorbent layer 6 disposed between the topsheet 3 and the backsheet 5. As shown in FIG. 2, the liquid absorbent layer 6 is of an almost rectangular shape. The liquid absorbent layer 6 has a front end edge 6a slightly inside the front end edge 1a of the sanitary napkin 1 and a rear end edge 6b slightly inside the rear end edge 1b of the sanitary napkin 1. The liquid absorbent layer 6 has transversely opposite side edges 6c inside rising bases 31 of the leakage preventing walls 30.

In the skin-side surface 2a, compressed grooves where the topsheet 3 and the liquid absorbent layer 6 are compressed are formed in the region between the leakage preventing walls 30, 30. As shown in FIG. 2, the compressed grooves comprise: longitudinal compressed grooves (primary longitudinal grooves) 11, 11 extending longitudinally in a curved manner; a front transverse compressed groove (front primary transverse groove) 12 located between front portions of the longitudinal compressed grooves 11, 11; and a rear transverse compressed groove (rear primary transverse groove) 13 connecting rear portions of the longitudinal compressed grooves 11, 11.

The region surrounded by the longitudinal compressed grooves 11, 11, the front transverse compressed groove 12, and the rear transverse compressed groove 13 is referred to as elongated main absorbent region 10. The main absorbent region 10 includes a front main absorbent region 10A, an intermediate main absorbent region 10B, and a rear main absorbent region 10D. The main absorbent region 10 has a length Ld of 150 to 300 mm as measured from a front end 10b to a rear end 10a.

In the front main absorbent region 10A, the right and left longitudinal compressed grooves 11, 11 are curved toward the longitudinal centerline Oy—Oy, wherein the distance between the longitudinal compressed grooves 11, 11 is smallest on the transverse reference line Ox—Ox. In the intermediate main absorbent region 10B, the longitudinal compressed grooves 11, 11 are curved away from the longitudinal centerline Oy—Oy. The rear main absorbent region 10D is elongated longitudinally of the napkin so that the distance between the longitudinal compressed grooves 11, 11 is smaller than in the intermediate main absorbent region 10B.

In the main absorbent region 10, a bulky, liquid permeable layer (cushion layer) 7 of a lower density than the liquid absorbent layer 6 is disposed between the topsheet 3 and the liquid absorbent layer 6, as shown in FIG. 3. As a result, the skin-side surface 2a of the main body 2 is raised more in the main absorbent region 10 than in the surrounding region, as shown in FIG. 1.

As shown in FIG. 2, the compressed grooves further comprise: a first outside transverse compressed groove (first auxiliary transverse groove) 14; a second outside transverse compressed groove (second auxiliary transverse groove) 16; first outside longitudinal compressed grooves (first auxiliary longitudinal grooves) 21, 21; and second outside longitudinal compressed grooves (second auxiliary longitudinal grooves) 22, 22.

The first outside transverse compressed groove 14 is disposed forward of the front transverse compressed groove 12. The first outside transverse compressed groove 14 is curved forward and connects the right and left longitudinal compressed grooves 11, 11. The region surrounded by the front transverse compressed groove 12 and the first outside transverse compressed groove 14 is referred to as forward diffusion suppressing region 15.

The second outside transverse compressed groove 16 is disposed rearward of the rear transverse compressed groove 13. The longitudinal compressed grooves 11, 11, the rear transverse compressed groove 13, and the second outside transverse compressed groove 16 are connected together, and both the rear transverse compressed groove 13 and the second outside transverse compressed groove 16 are curved rearward. Here, the region surrounded by the rear transverse compressed groove 13 and the second outside transverse compressed groove 16 is referred to as rearward diffusion suppressing region 17.

On both right and left sides of the front main absorbent region 10A, the first outside longitudinal compressed grooves 21, 21 are disposed at a distance outwardly apart from the longitudinal compressed grooves 11, 11. The first outside longitudinal compressed grooves 21, 21 are also curved toward the longitudinal centerline Oy—Oy, wherein the distance therebetween is smallest on the transverse reference line Ox—Ox.

On both right and left sides of the rear main absorbent region 10D, the second outside longitudinal compressed grooves 22, 22 are disposed at a distance transversely apart from the longitudinal compressed grooves 11, 11. The second outside longitudinal compressed grooves 22, 22 extend longitudinally in substantially parallel relation to the longitudinal centerline Oy—Oy, wherein front ends 22a, 22a are located at a boundary between the intermediate main absorbent region 10B and the rear main absorbent region 10D and rear ends 22b, 22b are located farther rearward of the second outside transverse compressed groove 16. That is, the rear main absorbent region 10D as a whole lies side-by-side with front portions of the second outside longitudinal compressed grooves 22, 22.

The rear ends 22b, 22b of the second outside longitudinal compressed grooves 22, 22 are located slightly inside the rear end edge 1b of the main body 2 but not spaced more than 20 mm apart forward from the rear end edge 6b of the liquid absorbent layer 6.

In the main body 2 of the sanitary napkin 1, the region from the rear end 10a of the main absorbent region 10 to the rear end edge 1b of the main body 2 is referred to as rear region 18. The rear region 18 includes the rearward diffusion suppressing region 17. The liquid absorbent layer 6 is located between the right and left leakage preventing walls 30, 30 and extends rearward farther than a rear end 17a of the rearward diffusion suppressing region 17. In the rear region 18, a length L0 from the rear end 10a of the main absorbent region 10 to the rear end edge 6b of the liquid absorbent layer 6 is preferably equal to or greater than 50 mm, more preferably equal to or greater than 70 mm. On the other hand, a length L2 from the rear end 17a of the rearward diffusion suppressing region 17 to the rear end edge 6b of the liquid absorbent layer 6 is preferably equal to or greater than 30 mm, more preferably equal to or greater than 40 mm.

Here, L1/L0 is preferably equal to or greater than ⅔ and equal to or less than 1, more preferably equal to or greater than ¾, where L1 represents a length from the rear end 10a of the main absorbent region 10 to the rear ends 22b of the outside longitudinal compressed grooves 22. Likewise, L3/L2 is preferably equal to or greater than ⅔ and equal to or less than 1, more preferably equal to or greater than ¾, where L3 represents a length from the rear end 17a of the rearward diffusion suppressing region 17 to the rear ends 22b of the outside longitudinal compressed grooves 22.

The individual compressed grooves are formed by heating the topsheet 3 and the liquid absorbent layer 6 under pressure from the side of the topsheet 3. At the bottoms of the individual compressed grooves, high-density compressed portions (highly compressed portions) and medium-density compressed portions (portions whose density is slightly lower than the high-density compressed portions) alternate with each other along the linear pattern of the compressed grooves so that the grooves are of a sufficient depth overall. The individual compressed grooves may be replaced by dot-like compressed portions arranged along the linear pattern at spaced intervals.

As shown in FIGS. 3 and 4, the side sheet 4 has an edge 4a coinciding with the outer edge of the backsheet 5. The side sheet 4 has a single-layer portion and a multi-layer portion, wherein the single-layer portion is bonded to the backsheet 5 or other materials disposed on the backsheet 5, whereas the multi-layer portion forms the leakage preventing wall 30 (see FIG. 3) or a stacked/fixed portion 37 (see FIG. 4). In the multi-layer portion, at first, the side sheet 4 is folded on its fold line 4b to have an edge 4c on the topsheet 3. In FIG. 3, the side sheet 4 is bonded to the topsheet 3 from the rising base 31 to the edge 4c.

Confronting surfaces of the side sheet 4 thus folded in two are bonded together through a hot-melt type adhesive with a plurality of elastic members 32, 33 disposed therebetween. The individual elastic members 32, 33 extend longitudinally over the entire length of the leakage preventing wall 30 and beyond the front and rear ends 30a, 30b. The elastic members 32, 33 are bonded to the side sheet 4 while being longitudinally stretched to a predetermined degree.

In an area of a length Lb from a rear bond edge 36 to the rear end edge 1b (see FIG. 2), the multi-layer portion of the side sheet 4 previously folded in two is further folded in three, as shown in FIG. 4, wherein these layers are bonded to each other as well as to the topsheet 3, thereby forming the stacked/fixed portion 37. Also in an area of a length Lc from a front bond edge 35 to the front end edge 1a, the multi-layer portion of the side sheet 4 is similarly folded and bonded, forming the stacked/fixed portion 37.

The front bond edge 35 and the rear bond edge 36 extend obliquely with respect to both the longitudinal direction and the transverse direction. Between the front bond edge 35 and the rear bond edge 36, the multi-layer portion of the side sheet 4 previously folded in two forms the leakage preventing wall 30 that can rise from the skin-side surface 2a, as shown in FIG. 3. It should be noted that the front end 30a of the leakage preventing wall 30 refers to one end of the front bond edge 35 that is closer to the front end edge 1a, and the rear end 30b of the leakage preventing wall 30 refers to one end of the rear bond edge 36 that is closer to the rear end edge 1b. The length of the leakage preventing wall 30 refers to a dimension La from the front end 30a to the rear end 30b.

The elastic members 32, 33 exert an elastic contractive force between the front end 30a and the rear end 30b, so that an elastic force acts to bring the front end 30a and the rear end 30b closer to each other, whereby the main body 2 is curved as shown in FIG. 1 and each leakage preventing wall 30 is raised from the skin-side surface 2a between the front end 30a and the rear end 30b.

Because the side sheet 4 at the stacked/fixed portion 37 is folded in a multi-layer structure and then bonded and fixed as shown in FIG. 4, the leakage preventing wall 30 includes: a lower inclined panel 30A extending obliquely upward from the rising base 31 toward the outside; an intermediate inclined panel 30B extending obliquely upward from the upper end of the lower inclined panel 30A toward the longitudinal centerline Oy—Oy; and a skin-contacting panel 30D extending obliquely upward from the upper end of the intermediate inclined panel 30B toward the outside, as shown in the half sectional view of FIG. 3.

Along the transverse reference line Ox—Ox, fold-back flaps 41 are disposed to project transversely outward from the main body 2. Each fold-back flap 41 extends over a given length with center at the transverse reference line Ox—Ox. Rearward of the fold-back flaps 41 are disposed rear flaps 42 also projecting transversely outward from the main body 2; forward of the fold-back flaps 41 are disposed front flaps 43 projecting transversely outward from the main body 2. Since the sanitary napkin 1 has bilateral symmetry about the longitudinal centerline Oy—Oy, the right and left flaps are of symmetrical shape.

The fold-back flap 41 has a side edge 41a that is gently curved transversely outward, wherein the half-width from the longitudinal centerline Oy—Oy to the side edge 41a of the fold-back flap 41 is largest on the transverse reference line Ox—Ox.

The rear flap 42 provides an almost constant half-width within the area of a length L4. That is, the rear flap 42 in this area has a side edge 42a that is substantially parallel to the longitudinal centerline Oy—Oy. Here "substantially parallel to the longitudinal centerline Oy—Oy" means that the side edge 42a extends with a deviation within a range of ±5 mm transversely from an imaginary parallel line Lh parallel to the longitudinal centerline Oy—Oy. In the present embodiment in which the side edge 42a is slightly curved outward as shown in FIG. 2, therefore, the side edge 42a extends outside the imaginary parallel line Lh but without deviation of greater than 5 mm therefrom. Of course, the side edge 42a may be parallel to the longitudinal centerline Oy—Oy without any deviation. Here, the half-width from the longitudinal centerline Oy—Oy to the imaginary parallel line Lh is larger than the half-width in the fold-back flap.

In the present embodiment in which the side edge 42a is substantially parallel to the longitudinal centerline Oy—Oy over the length L4, the rear flap 42 has an appropriate width although extending over a large area.

Preferably, a length L5 from the transverse reference line Ox—Ox to the front end of the side edge 42a falls within the range of 80 to 150 mm.

In the sanitary napkin 1, front pressure-sensitive adhesive layers 51, first rear pressure-sensitive adhesive layers 52, second rear pressure-sensitive adhesive layers 53, and central pressure-sensitive adhesive layers 54 are disposed on the garment-side surface, as shown in FIG. 2. In the fold-back flap 41, the front pressure-sensitive adhesive layer 51 is disposed on the backsheet 5. In the rear flap 42, the first and second rear pressure-sensitive adhesive layers 52, 53 longitudinally spaced apart from each other are disposed on the backsheet 5. In the region between the leakage preventing walls 30, the central pressure-sensitive adhesive layers 54 given the shape of a longitudinally extending strip are disposed on the backsheet 5.

In the fold-back flap 41, as shown in FIGS. 2, 3 and 4, a reinforcing sheet 56 is interposed between and bonded to the backsheet 5 and the side sheet 4. Also in the rear flap 42, a reinforcing sheet 57 is interposed between and bonded to the backsheet 5 and the side sheet 4.

When folded back against the outer surface of the crotch part of the undergarment, the fold-back flap 41 thus reinforced with the reinforcing sheet 56 may be certainly fixed to the outer surface of the crotch part without twisting. The rear flap 42 in a developed state may also be fixed to the inner surface of the undergarment without twisting.

The reinforcing sheets 56, 57 may be formed of the same material to have the same thickness, or maybe formed of different materials to have different thicknesses. Particularly when the reinforcing sheet 57 in the rear flap 42 is formed of a sheet capable of absorbing and retaining liquid, menstrual blood trying to ooze through between the side sheet 4 and the backsheet 5 can be retained by the reinforcing sheet 57.

When materials similar to the backsheet 5, the reinforcing sheet 56 or 57 and the side sheet 4 are stacked one on another, bonded to each other through a similar adhesive, cut into a sample of 65×65 mm, and then bent to a maximum curvature of ±2.5 $cm^{-1}$ with "Pure Bending Tester: KES-FB2" manufactured by Kato Tech Co., Ltd., the bending stiffness preferably falls within the range of 0.1 to 1.5 mN·$cm^2$/cm, while the bending recovery preferably falls within the range of 0.03 to 1.5 mN·cm/cm.

Here, the bending stiffness is a value obtained by differentiating a bending moment per 1 cm width of the sample with respect to the maximum curvature, while the bonding recovery is a difference in hysteresis curve between a bending moment when the sample is bent from one side to the maximum curvature and a bending moment when the sample is bent from the other side to the maximum curvature.

Within the foregoing ranges, the fold-back flaps 41 and the rear flaps 42 may hardly twist but may be soft enough to prevent an uncomfortable feeling.

Next, preferred examples of the individual components of the sanitary napkin 1 will be described.

The topsheet 3 is a liquid-permeable sheet, such as a through-air bonded nonwoven fabric, a spunlaced nonwoven fabric, or an apertured resin film (resin film formed with a large number of liquid passage holes). The backsheet 5 is a resin film that is impermeable to liquid but may be breathable.

The liquid absorbent layer 6 may be a layer of pulp, a layer of pulp and superabsorbent polymer, or an air-laid nonwoven fabric in which only pulp or pulp and rayon are deposited by air-laid process and the fibers are fixed together through an adhesive. The liquid permeable layer 7 is a bulky nonwoven fabric of a three-dimensional network structure, such as a through-air bonded nonwoven fabric or an air-laid nonwoven fabric in which pulp and synthetic fibers are deposited by air-laid process and the fibers are fixed together through an adhesive.

The side sheet 4 is impermeable to liquid and is preferably treated to be water-repellent. The side sheet 4 may be a meltblown nonwoven fabric, a spunbonded nonwoven fabric, or a laminated composite of spunbond/meltblown/spunbond.

The side sheet 4, which forms the leakage preventing wall 30 and appears on the skin-side surface of the napkin outside the leakage preventing wall 30, preferably exerts some degree of frictional force against the wearer's skin. With such a frictional force, the rear flap 42 may hardly slip on the wearer's skin, so that even when the rear main absorbent region 10D is deformed to fit in the cleft of the buttocks, the rear flap 42 is hardly deformed to come closer to the longitudinal centerline Oy—Oy.

In order to let the side sheet exert such a frictional force, a meltblown nonwoven fabric made of ethylene alpha-olefin copolymer resin may be used for the side sheet 4, or a rubber-based hot-melt pressure-sensitive adhesive not containing a tackifier ingredient may be applied to the surface of the side sheet 4.

The reinforcing sheets 56, 57 may be of a spunbonded nonwoven fabric, a point-bonded nonwoven fabric, a meltblown nonwoven fabric, or a paper material. In order that the reinforcing sheet 57 in the rear flap 42 may exhibit the ability to absorb and retain liquid, the reinforcing sheet 57 may be of a pulp sheet, an absorbent paper manufactured by wet papermaking process and then creped, an air-laid pulp in which pulp is deposited by air-laid process and then bonded together through an adhesive, or an air-laid nonwoven fabric in which pulp and thermoplastic synthetic fibers are deposited by air-laid process and then bonded together through an adhesive.

The pressure-sensitive adhesive layers 51, 52, 53 and 54 may be of a rubber-based hot-melt type adhesive.

The sanitary napkin 1 is to be worn with the intersection of the longitudinal centerline Oy—Oy and the transverse reference line Ox—Ox almost coinciding with the center of the woman's vaginal opening. Here, the fold-back flaps 41 projecting into the leg openings of the undergarment are folded back against the outer surface of the crotch part and adhered thereto through the front pressure-sensitive adhesive layers 51 disposed on the fold-back flaps 41. In addition, the garment-side surface 2b of the main body 2 of the sanitary napkin 1 is adhered to the inner surface of the undergarment, from the crotch part to the lower part of the back body, through the central pressure-sensitive adhesive layers 54.

Furthermore, the rear flaps 42 in a developed state are placed on the inner surface of the undergarment at the lower part of the back body and their garment-side surfaces are adhered to the inner surface of the undergarment through the first rear pressure-sensitive adhesive layers 52 and the second rear pressure-sensitive adhesive layers 53.

In the sanitary napkin 1, the skin-side surface 2a is recessed as shown in FIG. 1 due to the longitudinal elastic contractive force of the leakage preventing walls 30, whereby the leakage preventing walls 30 are raised from the skin-side surface 2a.

When worn, the longitudinal central portion of the front main absorbent region 10A, i.e., the intersection of the longitudinal centerline Oy—Oy and the transverse reference line Ox—Ox and its surrounding area may confront the woman's vaginal opening. Since the thighs exert a pressure transversely on the front main absorbent region 10A placed on the inner surface of the crotch part of the undergarment, the front main absorbent region 10A may easily be deformed to bulge toward the wearer's body and brought into close contact with the vaginal opening.

On the other hand, the intermediate portion between the front main absorbent region 10A and the intermediate main absorbent region 10B may confront the perineum, and the front portion of the intermediate main absorbent region 10B may confront the anus. Accordingly, the rear main absorbent region 10D may extend along the cleft of the buttocks and the rear portion of the rear main absorbent region 10D, i.e., the portion within about 5–20 mm forward from the rear end 10a of the main absorbent region 10 may confront the coccyx.

When subjected to a tightening force of the undergarment, the intermediate main absorbent region 10B and the rear main absorbent region 10D may be deformed to fit in the cleft of the buttocks. At the same time, the rear flaps 42, 42 disposed on each side of the rear main absorbent region 10D and the rear region 18 disposed rearward of the rear end 10a of the main absorbent region 10 may be deformed to conform to the surfaces of the buttocks.

Here, the rear region 18 extends rearward from the rear transverse compressed groove 13 over a length of equal to or greater than 50 mm, preferably equal to or greater than 70 mm. In a region extending rearward from the second outside transverse compressed groove 16 over a length of equal to or greater than 30 mm, preferably equal to or greater than 50 mm, additionally, no compressed groove is provided adjacent the longitudinal centerline Oy—Oy. Therefore, the rear region 18 can easily be deformed to conform to the curved surfaces of the buttocks.

In addition, since the second outside longitudinal compressed grooves 22, 22, which extend parallel with the longitudinal direction on each side of the longitudinal centerline Oy—Oy, may function as flexible hinges in the rear region 18, facilitating deformation. Therefore, the rear region 18 may easily be brought into close contact with the surfaces of the buttocks. Since a space is hardly formed between the rear region 18 and the surfaces of the buttocks, rearward leakage of liquid can be easily prevented.

Even if a space is left between the skin-side surface 2a of the main body 2 and the wearer's body, the leakage preventing walls 30, 30, which are allowed to rise outside the side edges 6c, 6c of the liquid absorbent layer 6, can block transverse liquid flow. Although the leakage preventing walls 30 longitudinally exert an elastic contractive force on the main body 2, the elastic contractive force hardly acts on the rear region 18 because the rear ends 30b of the leakage preventing walls 30 are located at substantially the same longitudinal position as the rear end 10a of the main absorbent region 10. Therefore, the rear region 18, which will hardly be affected by the elastic contractive force, can easily conform to the surfaces of the buttocks.

The liquid absorbent layer 6 extending over a large area in the rear region 18 is not only fixed between the topsheet 3 and the backsheet 5 through an adhesive but also integrated with the topsheet 3 through formation of the second outside longitudinal compressed grooves 22, 22. Therefore, even when body movement during sleep exerts a force that will try to displace or wrinkle the liquid absorbent layer 6 in the rear region 18, the liquid absorbent layer 6 will not be badly deformed. As a result, the rear region 18 including the liquid absorbent layer 6 can be kept in close contact with the buttocks, hardly giving an unpleasant feeling to the buttocks.

Body liquid such as menstrual blood discharged from the vaginal opening may pass through the topsheet 3 and the liquid permeable layer 7 mainly in the front main absorbent region 10A for subsequent absorption by the liquid absorbent layer 6. Body liquid such as menstrual blood trying to spread in all directions inside the topsheet 3 or the liquid absorbent layer 6 may be drawn into the high-density compressed grooves surrounding the main absorbent region 10 and then diffused along the compressed grooves, effectively preventing liquid diffusion out of the main absorbent region 10.

Body liquid such as menstrual blood applied to the front main absorbent region 10A may sometimes spread to the rear main absorbent region 10D. Moreover, menstrual blood trying to flow down the wearer's body from the anus to the cleft of the buttocks may pass through the topsheet 3 and the liquid permeable layer 7 in the intermediate main absorbent region 10B and the rear main absorbent region 10D for subsequent absorption by the liquid absorbent layer 6. However, since the rear main absorbent region 10D is surrounded by the longitudinal compressed grooves 11, 11 and the rear transverse compressed groove 13, the menstrual blood hardly reaches the rear region 18.

Here, the rear end 10a of the main absorbent region 10 is spaced at least 50 mm apart from the rear end edge 6b of the liquid absorbent layer 6, and the white color of the liquid absorbent layer 6 may be seen through the topsheet 3 in the rear region 18. In the case, therefore, even when menstrual blood diffused in the rear main absorbent region 10D is seen through the topsheet 3, the sanitary napkin will not look as if a large amount of menstrual blood was applied thereto and hardly cause a wearer anxiety about rearward leakage of menstrual blood.

In the sanitary napkin 1 according to the present invention, moreover, the rearward diffusion suppressing region 17 surrounded by the compressed grooves is provided rearward of the rear end 10a of the main absorbent region 10. Therefore, even if menstrual blood flowing down the wearer's body crosses the rear end 10a of the main absorbent region 10, the menstrual blood may be retained in the rearward diffusion suppressing region 17 and prevented from diffusing farther rearward.

Figure 5:
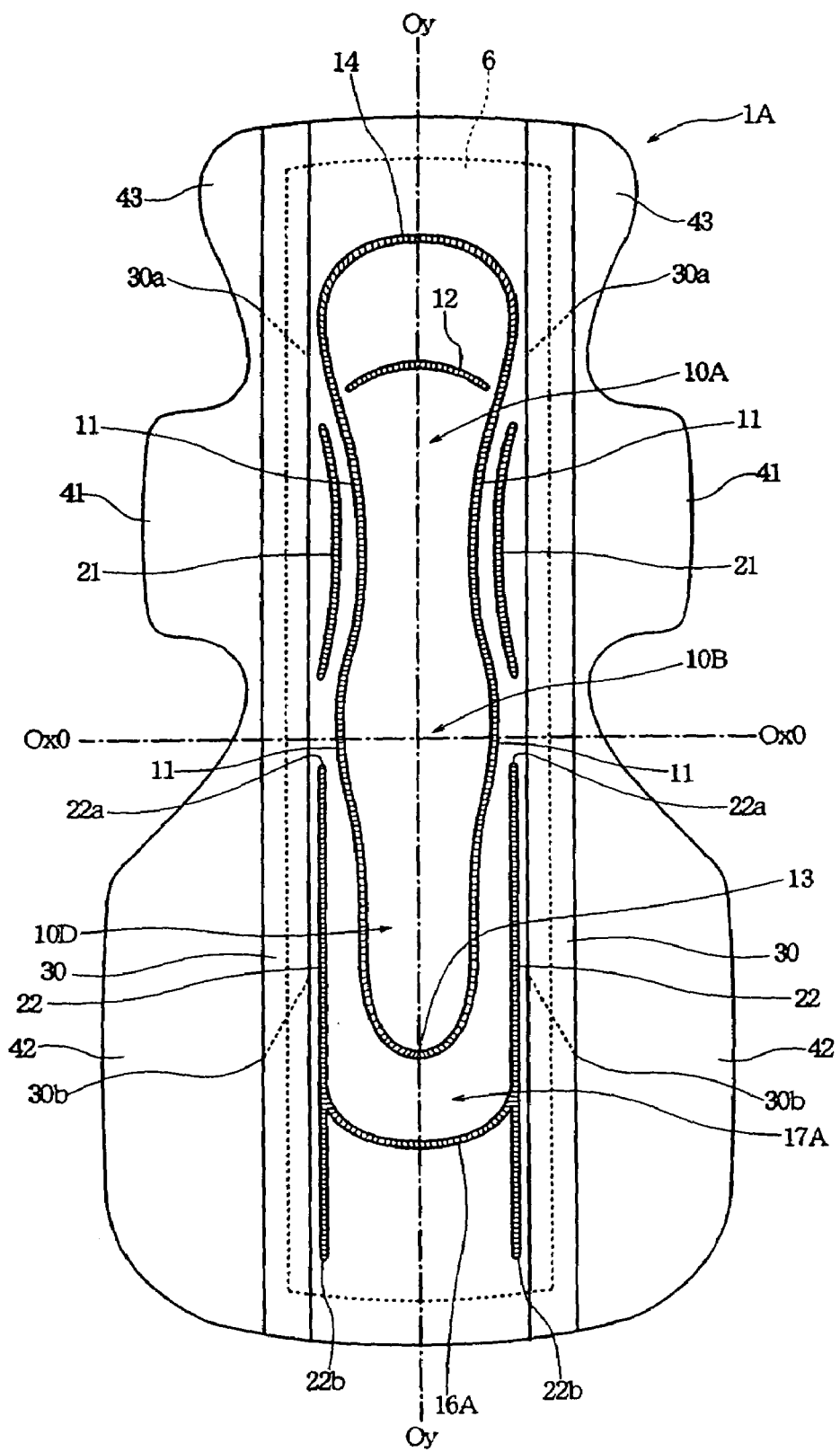
FIG. 5 is a top plan view of a sanitary napkin according to a second embodiment of the present invention.

FIG. 5 is a top plan view showing a sanitary napkin 1A according to a second embodiment of the present invention.

The sanitary napkin 1A is similar to the sanitary napkin 1 shown in FIG. 2, except that the pattern of the compressed grooves formed in the skin-side surface 2a is modified only partially.

The difference is such that a second outside transverse compressed groove 16A disposed rearward of the rear transverse compressed groove 13 is formed to connect second outside longitudinal compressed grooves 22A, 22A disposed outside thereof so that a rearward diffusion suppressing region 17A is of U-shape defined by the rear transverse compressed groove 13, the second outside transverse compressed groove 16A, the longitudinal compressed grooves 11, and the second outside longitudinal compressed grooves 22, as shown in FIG. 5. The remaining constructions, preferred dimensions, and preferred dimensional relationships are not changed from those in the sanitary napkin 1.

According to the present invention, as has been described hereinabove, since the main absorbent region defined by the compressed grooves is at an appreciable distance apart from the rear end edge of the main body, body liquid such as menstrual blood hardly diffuses close to the rear end edge, so that the appearance will not cause anxiety about leakage. Furthermore, since the rear region is formed with the auxiliary longitudinal grooves where the liquid absorbent layer is compressed, the liquid absorbent layer in the rear region will not be badly deformed.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the features set out in the appended claims.

What is claimed is:

1. A sanitary napkin comprising:
   an elongated main body having a skin-side surface and a garment-side surface and including a liquid-permeable topsheet appearing on the skin-side surface, a backsheet appearing on the garment-side surface, and a liquid absorbent layer disposed between the topsheet and the backsheet;
   leakage preventing walls disposed at substantially equal distances on each side of a longitudinal centerline of the main body and extending longitudinally of the main body, the leakage preventing walls exhibiting an elastic contractive force so as to rise from the skin-side surface; and
   compressed grooves, where the liquid absorbent layer is compressed together with the topsheet, being formed in a region of the main body between the leakage preventing walls, the compressed grooves comprising:
      primary longitudinal grooves disposed at substantially equal distances on each side of the longitudinal centerline of the main body, the primary longitudinal grooves extending longitudinally of the main body and defining a main absorbent region therebetween;
      a primary transverse groove disposed between rear portions of the primary longitudinal grooves, the primary transverse groove extending transversely of the main body and defining a rear end of the main absorbent region; and
      auxiliary longitudinal grooves disposed at substantially equal distances on each side of the longitudinal centerline of the main body, wherein
   the liquid absorbent layer has a rear end edge in a rear region that extends rearward from the rear end of the main absorbent region to a rear end edge of the main body, and the auxiliary longitudinal grooves extend longitudinally of the main body from regions transversely adjacent the main absorbent region to the rear region so that the auxiliary longitudinal grooves in the rear region are transversely spaced more than the primary longitudinal grooves,
   the compressed grooves further comprise an auxiliary transverse groove disposed rearward of the primary transverse groove and between the auxiliary longitudinal grooves, wherein a rearward diffusion suppressing region rearward of the rear end of the main absorbent region is defined between the primary transverse groove and the auxiliary transverse groove, and the auxiliary longitudinal grooves have rear ends rearward of a rear end of the rearward diffusion suppressing region.

2. A sanitary napkin according to claim 1, wherein the individual auxiliary longitudinal grooves in the rear region extend parallel to the longitudinal centerline.

3. A sanitary napkin according to claim 1, wherein rear ends of the leakage preventing walls are located at substantially the same longitudinal position as or forward of the rear end of the main absorbent region.

4. A sanitary napkin according to claim 1, wherein rear ends of the leakage preventing walls are located at substantially the same longitudinal position as or forward of the rear end of the rearward diffusion suppressing region.

5. A sanitary napkin according to claim 1, further comprising:
   fold-back flaps projecting outward from transversely opposite sides of the main body and configured to be folded back against and fixed to an outer surface of an undergarment at a crotch part thereof; and
   rear flaps located rearward of the fold-back flaps, projecting outward from the transversely opposite sides of the main body to be placed on an inner surface of the undergarment in an unfolded state, wherein
   the rear flaps are located outside the auxiliary longitudinal grooves.

6. A sanitary napkin according to claim 1, wherein $L1/L0$ is at least $2/3$, where $L0$ represents a length from the rear end of the main absorbent region to the rear end edge of the liquid absorbent layer while $L1$ represents a length from the rear end of the main absorbent region to the rear ends of the auxiliary longitudinal grooves.

7. A sanitary napkin according to claim 6, wherein $L0$ is equal to or greater than 50 mm.

* * * * *